US007387616B2

(12) United States Patent
Li

(10) Patent No.: US 7,387,616 B2
(45) Date of Patent: Jun. 17, 2008

(54) SAFE MEDICAL NEEDLE APPARATUS

(75) Inventor: Junsheng Li, Shanghai (CN)

(73) Assignee: Shanghai Kindly Enterprise Development Group Co. Ltd. (CN)

( * ) Notice: Subject to any disclaimer, the term of this patent is extended or adjusted under 35 U.S.C. 154(b) by 527 days.

(21) Appl. No.: 10/946,545

(22) Filed: Sep. 21, 2004

(65) Prior Publication Data
US 2005/0038384 A1 Feb. 17, 2005

Related U.S. Application Data

(63) Continuation of application No. PCT/CN03/00122, filed on Feb. 8, 2003.

(30) Foreign Application Priority Data

Mar. 29, 2002 (CN) ............................. 02 1 11197

(51) Int. Cl.
*A61M 5/00* (2006.01)
*A61M 5/178* (2006.01)
*A61M 5/32* (2006.01)
(52) U.S. Cl. ................ 604/198; 604/263; 604/164.08
(58) Field of Classification Search ................ 604/110, 604/164.11, 164.01, 197, 164.08, 195, 192, 604/198, 263, 264, 166.01
See application file for complete search history.

(56) References Cited

U.S. PATENT DOCUMENTS

| 5,300,045 A * | 4/1994 | Plassche, Jr. ............... 604/263 |
| 5,419,766 A | 5/1995 | Chang et al. |
| 5,683,365 A | 11/1997 | Brown et al. |
| 6,012,213 A | 1/2000 | Chang et al. |
| 6,221,047 B1 | 4/2001 | Greene et al. |
| 6,224,569 B1 | 5/2001 | Brimhall |
| 6,379,333 B1 * | 4/2002 | Brimhall et al. ....... 604/164.11 |

FOREIGN PATENT DOCUMENTS

CN 1108140 9/1995

\* cited by examiner

*Primary Examiner*—Matthew F. Desanto
(74) *Attorney, Agent, or Firm*—Dorsey & Whitney LLP; Min (Amy) S. Xu

(57) ABSTRACT

A safe medical needle apparatus, including a needle duct having a needle head, a needle seat, in which the needle tail is installed; a safe protecting shell and a biasing part through which the needle duct can pass; A protuberant stop portion, which is provided on the outer surface of the needle duct near the needle head, and the maximum size of cross section thereof is larger than the outer diameter of the remainder of the needle duct; the safe protecting shell there inside includes sequentially a biasing part cavity near the outlet, a protecting cavity, the across section of which is smaller than the biasing part cavity, a stop portion of the protecting shell and a needle seat cavity near the inlet of the needle duct and matching the needle seat; the size of the stop portion of the protecting shell is smaller than the maximum size of the stop portion of the needle duct, making the needle duct be movable therein but the stop portion of the needle duct be locked thereby, wherein a side of the biasing part cavity having a releasing port. Said biasing part is elastic and includes a through hole, under action of a external force the biasing part is contained in the biasing part cavity and is so biased that the needle duct can pass the through hole, and if the external force is removed, the through hole displaces and staggers with the needle duct under the action of the elasticity.

9 Claims, 6 Drawing Sheets

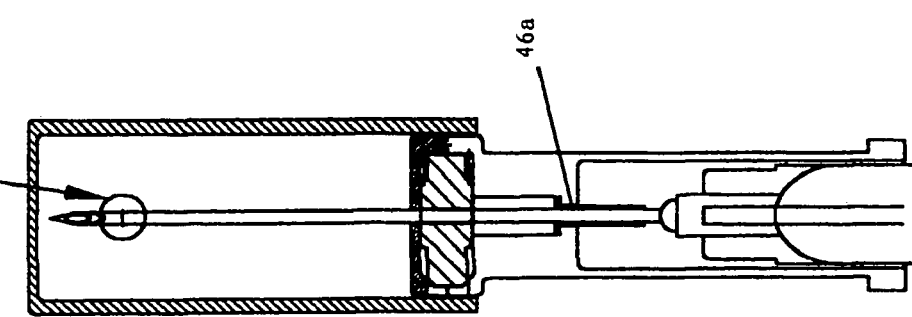
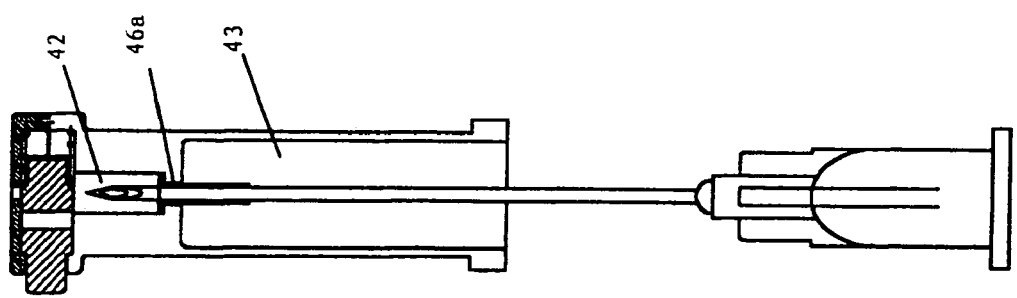
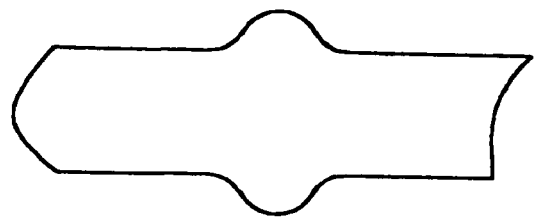
FIG. 2(a)   FIG. 2(b)   FIG. 2(c)

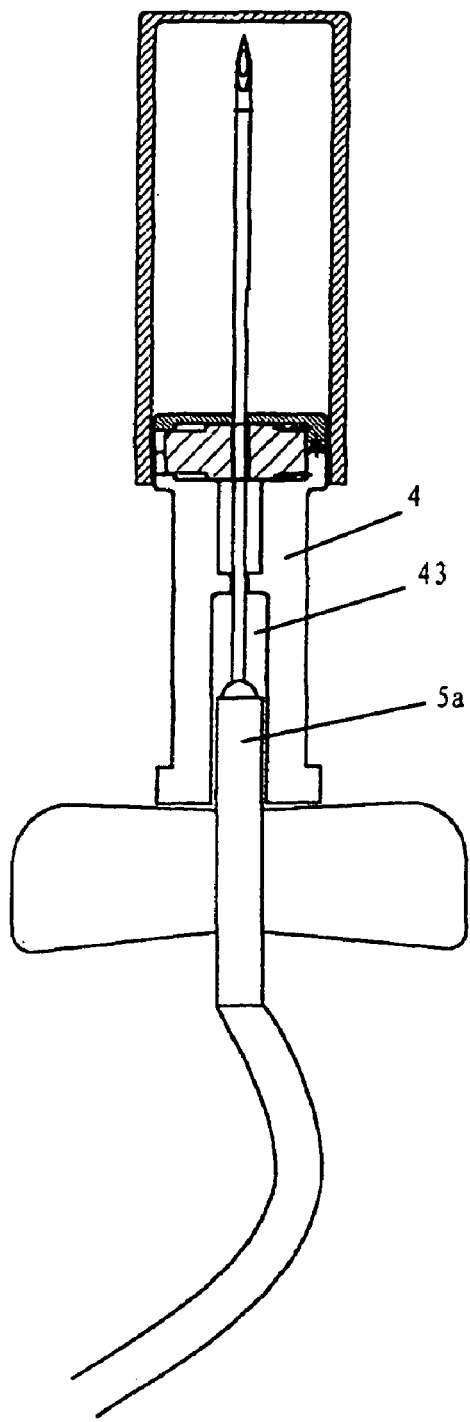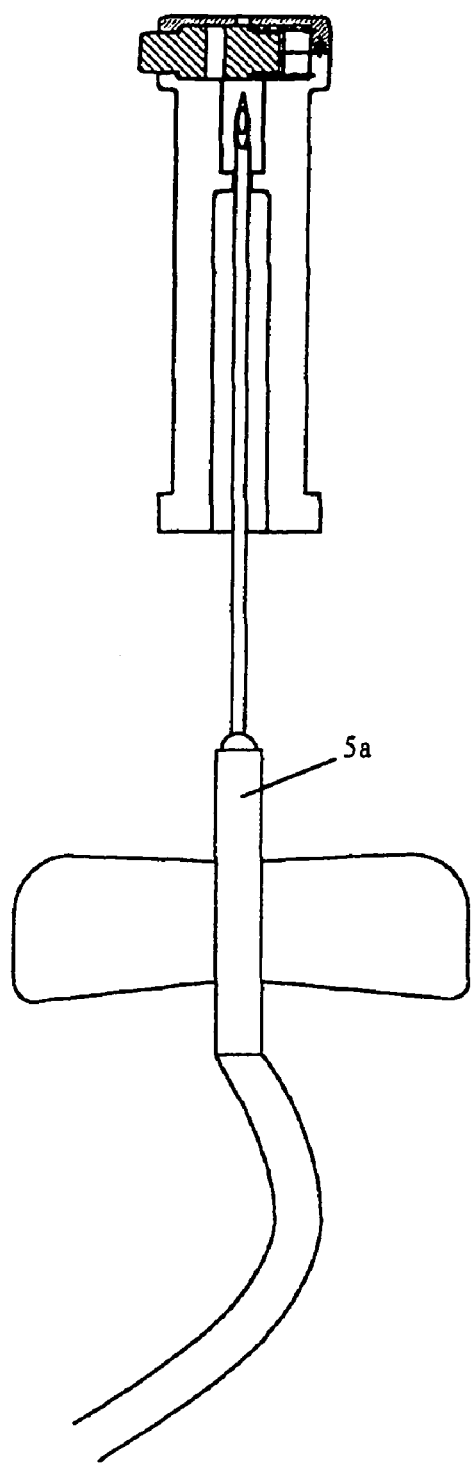
FIG. 3(a)        FIG. 3(b)

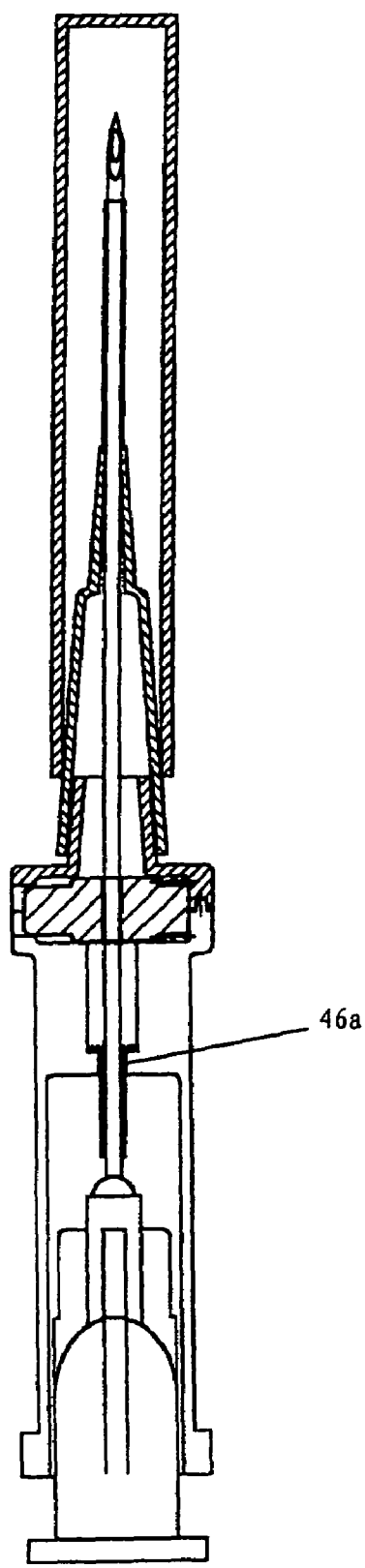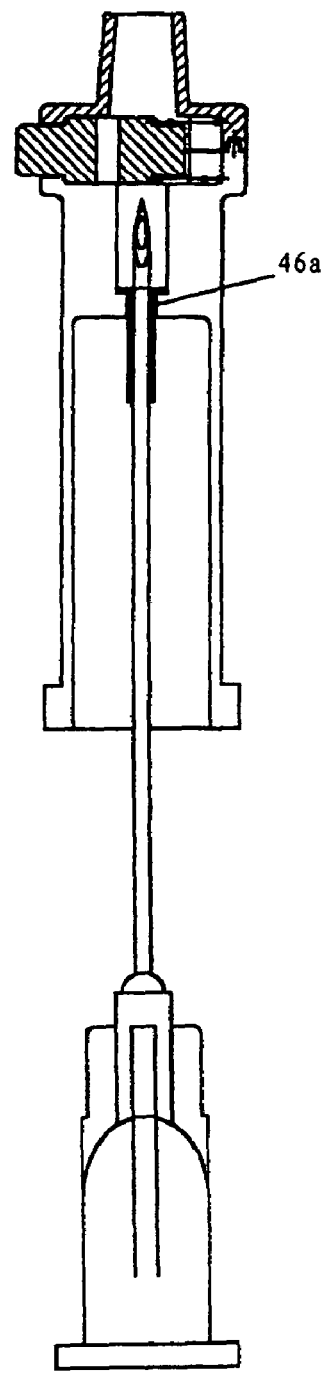
FIG. 6 (a)　　　　FIG. 6 (b)

SAFE MEDICAL NEEDLE APPARATUS

CROSS-REFERENCE TO RELATED APPLICATION(S)

This application is a continuation of International Application No. PCT/CN03/00122, filed on Feb. 8, 2003, which claims priority to Chinese Patent Application CN 02111197.9, filed on Mar. 29, 2002, the contents of which is incorporated herein in their entirety.

FIELD OF THE INVENTION

This invention relates to a medical needle, specially relates to a safe medical apparatus. The safe medical needle apparatus of the present invention is available in injector, medical blood collection and transfusion device, drug hypodermic needle, perfusion apparatus with wings, cannula indwelling needle and other products matching hollow needle head.

BACKGROUND OF THE INVENTION

Since adopting disposable medical instruments, a large number of waste instruments bring on the problem of environment pollution. Furthermore, the utilized instruments with needles frequently puncture-wound the medical workers, resulting in that the virus or bacteria carried by the bodies of the patients can infect the medical workers and causing the medical workers to be infected diseases even to be dead. These events are often heard in the worldwide. Currently, the problem of the unexpected puncture-wound is attended more and more due to the susceptibility of AIDS, hepatitides and other serious hematopathies.

Thus it can be seen that puncture-wounding the medical workers by the needle heads of the instruments with needles possesses huge danger. Accordingly, numerous apparatus have been provided for eliminating or decreasing this danger. At present, these apparatus can be produced in theory, but actually, many apparatus fail to adapt to be manufactured economically and reasonably in mass production and/or in low cost mainly because the adopted technologies and processes are too complex, for instance, existing the problem of molding tolerance.

U.S. Pat. No. 5,348,544 granted to Sweeney, et al., on Sep. 20, 1994 (simply referred to as "Sweeney's") has opened an injector apparatus involving a shield. The shield is slid by manual operation along the needle-head duct, from the position where it is near the operator to the far position where the needlepoint is covered. The apparatus includes an articulated arm, which protrudes from the needle-head duct and is movable away from the operator for self-folding, so that the shield protrudes and cover the needlepoint. A metal clip blocks the contact of the needlepoint. In addition, it further opened a substituting embodiment, wherein a spring assists the manual operation. The company Becton Dickinson located in Flankling Lake City of N.J. has sold an injector apparatus designed on the basis of the Sweeney's patent, which utilizes three separate parts (two molded parts and one metal clip) for moving the shield. Once the apparatus protrudes in order to cover the needlepoint, it is hard to be resetting. Therefore, the needle head is difficult to continue to be used. Furthermore, the articulated arm needs to be started at the area where the needle head is located and includes some parts. These parts will hinder the operator to watch the position where the needle shall penetrate.

U.S. Pat. No. 5,246,428 granted to Donaldw. Falknor (simply referred to as "Falknor's") on Sep. 21, 1993 has opened an injector apparatus involving a covering part, which can be released automatically to protrude in direction away from the operator, so as to cover the needle head. This apparatus includes a locking mechanism, which can be switched manually between the unlocking position and locking position, so as to expose the needle head for using and locking the covering part on the needle head. Of course, the positions of the locking mechanism provide the visual indication of the safety condition of the apparatus (whether the latch is fastened). However, this locking mechanism is a sole safety mechanism and the position indication thereof may be "lost" in the tensional circumstance. When the locking mechanism is at the unlocking position, if the front end impacts certain areas of the body, it will occur that the areas contact the needle head. In addition, the covering part can cover a portion of the connected injector body before the covering part wholly protrudes. Even if the covering part is made of transparent material, it is possible that the indicating mark of volume metering on the injector body is difficult to be red out accurately when the injector is used in the case of titration.

U.S. Pat. No. 5,256,153 granted to Lawrence W. Hake (simply referred to as "Hakes'") on Oct. 26, 1993 has opened an injector apparatus, which includes a shield slid by manual operation. The shield is located on the injector body in the process of medical treatment using the medical needle head of the injector and usually slides into the position where the needle head is protected in the direction away from the operator after finishing this course. The operators utilizing this apparatus usually complain that it is difficult to clearly view the metering indication mark when the shield is located on the injector body and there is a danger of unexpected puncture wound made by the needle head when the shield moves in direction away from the operator for covering the needle head. Furthermore, when the shield covers the needle head, it is hard to determine if the shield is in locking condition or unlocking condition, resulting to the possibility of unexpected puncture wound made by needle head.

U.S. Pat. Nos. 5,139,489 and 5,154,285 granted to William H. Hollister (simply referred to as "Hollister'") respectively on Aug. 18, 1992 and Oct. 13, 1992 have opened a needle head protecting apparatus, which can be applied in a assembly of cuspidal needle head having two ends or simpler single needle head system. This protecting apparatus includes a generally rigid shell, which flexibly join with a container used in a vacuum test tube sampling system or a needle head casing. When operating this protecting apparatus, the rigid shell pivots to the position where the exposed needle heads of the assembly of cuspidal needle head having two ends are joined and is reliably fixed on the exposed needle heads. One of the main defects existing in the Hollister's needle head protecting apparatus lies in the length size and position of the rigid shell. The length size and position of the rigid shell causes the inconvenience when some assemblies or systems are used in process of medical treatment, as considered by some peoples. The second defect is that it is need to either pivot the shell to join the needle head by two hands, or seek out and utilize a certain stably supporting surface to withstand the shell when the needle head pivots into the shell. In a structure of a currently sold product, a retainer of a certain integral container of the Hollister's apparatus includes two molded parts, which can make the shell pivot as far as possible to the position where the process of medical treatment is not hampered. This design needs five molded parts including a needle head assembly, which can be discarded.

U.S. Pat. No. 5,823,997 granted to David L. Thorne (simply referred to as "D L. Thorne'") on Oct. 20, 1998 has opened a collapsible scabbard for a needle head, in which the scabbard is folded around a medical needle head, allowing to operate the needle head in process of medical treatment. The scabbard in a point away from the sharp needle end is hinged on a structure, such as the needle head casing or bloodletting barrel. The needle end is enveloped last, so as to protect the operator. At the end of the process of medical treatment, the scabbard is unfolded and protrudes in the direction toward the needle end away from the structure, so as to envelop the needle head and the cuspidal needle end thereof, which the operator can not contact. According to the description made by D L. Thorne, an important object of the apparatus is to provide a scabbard, which is collapsible for use in the process of medical treatment adopting medical needle head and can be unfolded to join the needle head to form a structure of a generally rigid needle head casing, so as to prevent unexpected contacting the cuspidal needle end. But there are two defects existing in this apparatus. One defect lies in that its structure is more complex and machining mold and molding is too difficult when the bloodletting barrel or needle head casing is integrally mold-formed, the costs thereof is hard to be accepted. The second defect lies in that this apparatus fails to meet the requirement of detachability and interchangeability of the medical needle. As we usually known, the medical needles in a clinical use often need repeatedly detaching and installing. For example, the injector needs to change the needle head when dispensing and human injecting. This requires that the medical needle shall possess the detachability and interchangeability. The common medical needles possess this characteristic, but in the designs of safe medical needles or instruments, in order to meet the function for protecting the needle, the detachability and interchangeability of the medical needle is lost. This defect exists not only in the opened patents of Sweeney, Falknor, Hake, Hollister, and D L. Thorne, et al, but also in the most of the safe types patent designs. This is the one of the important reasons why such more patent designs are hard to be commercialized.

The U.S. Pat. No. 6,254,575 granted to Gale H. Torme (simply referred to as G H. Thorne's) on Jul. 3, 2001 has also opened an improved shield of a collapsible needle head, which is similar to the D L. Thorne's, but possesses the detachability and interchangeability in respect to the injecting needle. The defect thereof lies in that the structure is too complex, not only it is difficult to molding-process, but also the volume size thereof is too large due to having the requirement for the length after spreading the collapsible shield, being difficult to use in the hollow medical needle head apparatus of the transfusion device, the cannula indwelling needle.

Therefore, though the above apparatus in the prior art can prevent that the instruments with needles stab the operator after use, it is difficult to be widely used in the medical field due to the complex structure and the expensive cost of manufacture thereof. In addition, lacking function of the detachability and interchangeability between the apparatus and the common medical needles leads to high use cost and makes use of these apparatus be restricted.

SUMMARY OF THE INVENTION

Therefore, the object of the invention is to provide a safe medical needle apparatus, which has a simple structure, low manufacturing cost and better detachability and interchangeability and can be widely used in the medical instruments, which need matching needles. The object of the invention can be achieved by the following technical solution.

A safe medical needle apparatus, including a needle duct having a needle head and a needle tail, a needle seat, in which the needle tail is installed; and characterized in that:

It further includes a safe protecting shell through which the needle duct can pass and a biasing part through which the needle duct can pass;

A protuberant stop portion of the needle duct, which is provided on the outer surface of the needle duct near the needle head, and the maximum size of cross section thereof is larger than the outer diameter of the remainder of the needle duct;

One end of the safe protecting shell forms an outlet of the needle duct and the other end forms an inlet of the needle duct, the safe protecting shell includes a biasing part cavity near the outlet, a protecting cavity, the across section of which is smaller than the biasing part cavity and through which the needle head and the stop portion can remove, a stop portion of the protecting shell and a needle seat cavity near the inlet of the needle duct and matching the needle seat, sequentially between the outlet of the needle duct and inlet of the needle duct of the protecting shell; the size of the stop portion of the protecting shell is smaller than the maximum size of the stop portion of the needle duct, making the needle duct be movable therein but the stop portion of the needle duct be locked thereby, wherein a side of the biasing part cavity having a releasing port; and Said biasing part is elastic and includes a through hole in which the needle duct and the stop portion of the needle duct can remove, under action of a external force the biasing part is contained in the biasing part cavity and is so biased that the needle duct can pass the through hole, and if the external force is removed, the through hole displaces and staggers with the needle duct under the action of the elasticity.

Thus it can be seen that the safe medical needle apparatus of the present invention possesses the merits of simple structure, low cost, convenient and safe operation. Specially, this safe medical needle apparatus is so universal that it can be applied in injector, medical blood collection and transfusion device, hypodermic medical needle, perfusion apparatus including a wing, cannula indwelling needle and other products matching hollow needle head, so long as the protecting shell is provided, in which the front end thereof or the shape of the needle seat shell are slightly changed.

BRIEF DESCRIPTION OF THE DRAWINGS

The following detailed description to the present invention will be made in reference to the companying drawings, in which:

FIGS. 2(a)-(c) show a second embodiment of the present invention, which is a hypodermic medical needle similar to the first embodiment, except the stop portion of the protecting shell;

FIGS. 3(a)-(b) show a third embodiment of the present invention, which is a perfusion needle;

FIGS. 6(a)-(b) show a sixth embodiment of the present invention, which is an indwelling needle similar to the fifth embodiment, except the stop portion of the protecting shell.

DETAILED DESCRIPTION OF THE PREFERRED EMBODIMENTS

Figures 1A, 1B, 1C:
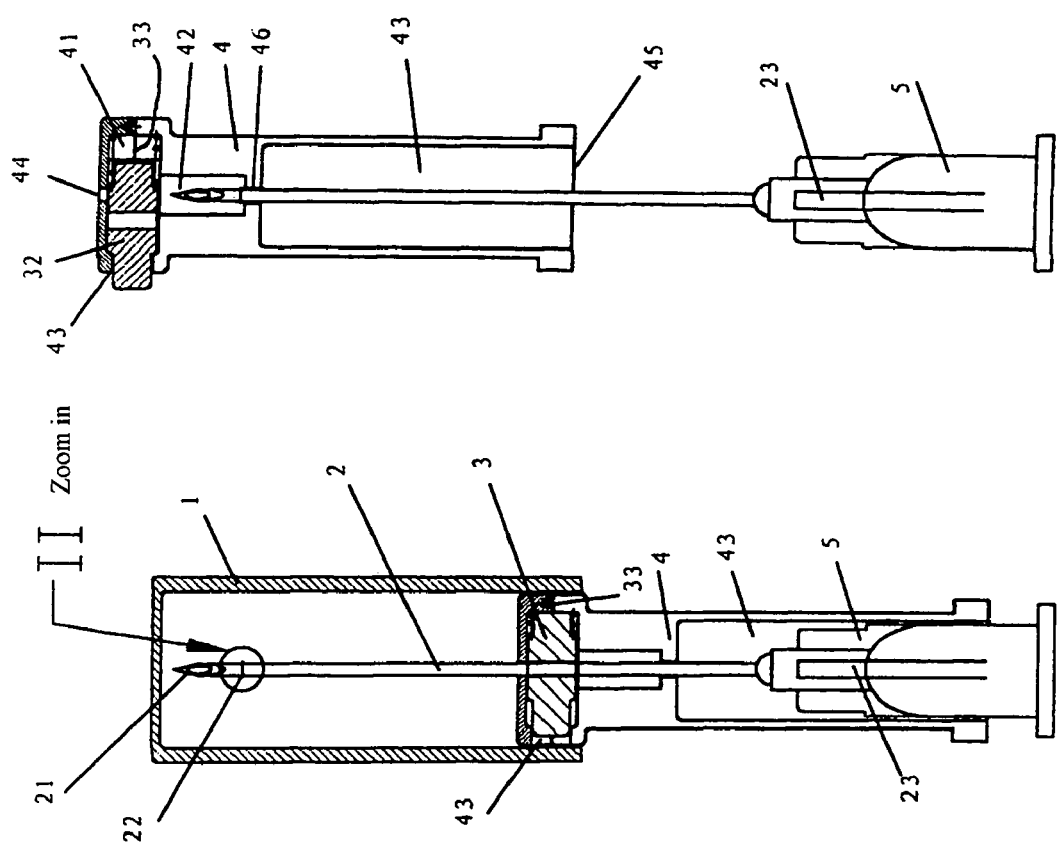
FIGS. 1(a)-(c) show a first embodiment of the present invention, which is a hypodermic medical needle.

As shown as in FIGS. 1(a)-(c), it is the first embodiment of a safe medical needle apparatus of the present invention, the injector includes a jacket 1, a needle duct 2, a biasing part 3, a safe protecting shell 4 and a needle seat 5.

Needle 2 includes a needle head 21 and a tail portion 23 inserting into the needle seat 5. The outer surface of the needle duct 2 near the needle head 21 forms a flange, the maximum size of which is larger than the outer diameter of the remainder of the needle duct, so as to form a stop portion 22. The flange can be of multifarious types, for example, the cross section thereof may be circular or not circular shape, such as, ellipse or sides of which at least have a protrusion, so long as the maximum size thereof is larger than the outer diameter of the needle duct.

The safe protecting shell 4 includes an outlet 44 at an end thereof in which the needle duct 2 including the stop portion 22 of the needle duct can pass through and an inlet 45 for the needle duct at the other end. There are three hollow cavities, which the needle duct 2 can pass through and are located between the outlet 44 and the inlet 45 for the needle duct of the protecting shell 4, i.e., in turn, being a biasing part cavity 41 near the outlet 44, thereafter a protecting cavity 42, the cross section thereof is smaller than the biasing part cavity 41, a stop portion 46 of the protecting shell and a needle seat cavity 43 near the inlet 45 for the needle duct. Wherein, the diameter of the protecting cavity 42 is larger than the outer diameter of the needle duct 2, so that the needle head 21 and the stop portion 22 of the needle duct can reciprocate therein. The diameter of the needle seat cavity 43 is set as the needle seat is reciprocated therein. The stop portion 46 of the protecting shell is set as a contracted neck portion provided between the protecting cavity 42 and the needle seat cavity 43. The inner diameter or the maximum size of the stop portion 46 is smaller than the maximum size of the stop portion 22 of the needle duct of the needle duct 2, so that the needle duct can reciprocate therein, but the stop portion 22 of the needle duct is locked and does not pass therethrough. A side of the biasing cavity 41 is provided with a release port 47.

An elastic biasing part 3 is contained in the biasing part cavity 41 of the protecting shell 4. The biasing part 3 forms a through hole 31, in which the needle duct including the stop portion 22 thereof can pass through. When the biasing part 3 is at the biasing condition, as shown in FIG. 1(a), under action of a an external force, for example, of the jacket 1, the needle duct 2 can pass through the through hole 31, or the through hole 31 and the needle duct 2 are aligned axially, allowing the needle duct 2 to pass through the hole 31. When the biasing part 3 is released, for example, the jacket 1 is removed, the through hole 31 staggers with the needle duct 2, as shown in FIG. 1(b), under the action of elasticity of the biasing part 3, so that the needle duct 2 cannot pass through the through hole 31. The body 32 of the biasing part 3 is made of an elastic material or non-elastic material. When the body 32 is made of a non-elastic material, the biasing part 3 further includes an elastic means, which is provided between the body 32 and the side-wall of the biasing part cavity 41, making the body 32 displace. As shown in FIG. 1(a), the elastic means is a spring 33 disposed on the sidewall of the biasing part cavity 41. When the body 32 is made of an elastic material, then it does not need the above spring 33.

The stalling and operating the safe medical needle of the present invention will be described in combination of the accompanied drawings as follows.

In the circumstance that the biasing part 3 adopts the body 32 made from the non-elastic material and an elastic means, such as spring 33 or elastomer, an external force applies on the release port of the biasing part cavity 41 and the spring 33 is compressed. In such condition, the outlet 44 of the safe protecting shell 4, the through hole 31 of the biasing part 3, the protecting cavity 42 of the safe protecting shell 4, the stop portion 46 and the needle seat cavity 43 are aligned axially and the needle duct 2 is inserted into the outlet 44 of the protecting shell 4. Then the needle tail 23 is installed on the needle seat 5 and finally the jacket 1 is set on the safe protecting shell 4 for protecting the needle head 21, as shown in FIG. 1(a). The protecting shell 4 is made perfectly of a transparent material for convenience of the assembling the medical needle.

Of course, the protecting shell also can be formed by two opposite half-opened pieces. Thus, firstly the needle duct 2 is inserted into the biasing part 3. Then the biasing part 3 provided with the needle duct 2 is placed in the biasing part cavity 41 of the protecting shell formed by two pieces. Finally, the protecting shell 4 is assembled as a whole.

When using an injector, the jacket 1 of the needle is removed. At the end of use, the safe protecting shell 4 is disengaged from the needle seat 5 and removed in the direction toward the needle head 21. When the needle head 21 and the stop portion 22 of the needle duct are disposed in the protecting cavity 42 of the protecting shell 4, the protecting shell 4 cannot be removed in a direction toward the needle head 21, as shown in FIG. 1(b), because the maximum size of outer flange of the stop portion 22 of the needle duct is larger than the inner diameter of the stop portion 46 of the protecting shell. Simultaneously, because the needle duct 2 is disengaged from the body 32 of the biasing part 3 of the body 32 of the biasing part displaces from the release port under the action of an elastic force of the spring 33, whereby the through hole 31 of the biasing part 3 is not aligned with the needle duct 2. Thus, the needle head 21 of the needle duct 2 is restricted within the protecting cavity 42 of the protecting shell 4, i.e., the needle head 21 will not be exposed outside of the safe protecting shell 4.

FIGS. 2(a)-(c) show a second embodiment of the present invention. As shown in these figures, except the stop portion 46a of the protecting shell, the remainders thereof are as same as ones in the embodiment shown in FIGS. 1(a)-(c), so here the description to the same parts will be omitted. In this embodiment, there is between the protecting cavity 42 and the needle seat cavity 43 a contracted neck portion similar to the one of the stop portion 46 of protecting shell in the first embodiment. The difference is that the diameter of the contracted neck portion of the second embodiment is larger than the one of the stop portion 46 of the needle duct, and a sleeve 46a having a turndown side is set out on the contracted neck portion. The diameter and the function of the sleeve 46a having a turndown side are respectively same as the ones of the stop portion 46 of the needle duct in the first embodiment.

FIGS. 3(a)-(b) show a third embodiment similar to the first embodiment of the present invention. The injecting needle matched to the injector of the first embodiment is generally used in subcutaneous injecting drugs. If the needle seat cavity 43 of the safe protecting shell 4 of this embodiment is changed to adapt the needle seat 5a of the perfusion device, the medical needle of the present invention can be used for the perfusion needle, as shown in FIGS. 3(*a*)-(*b*).

Figure 4A:
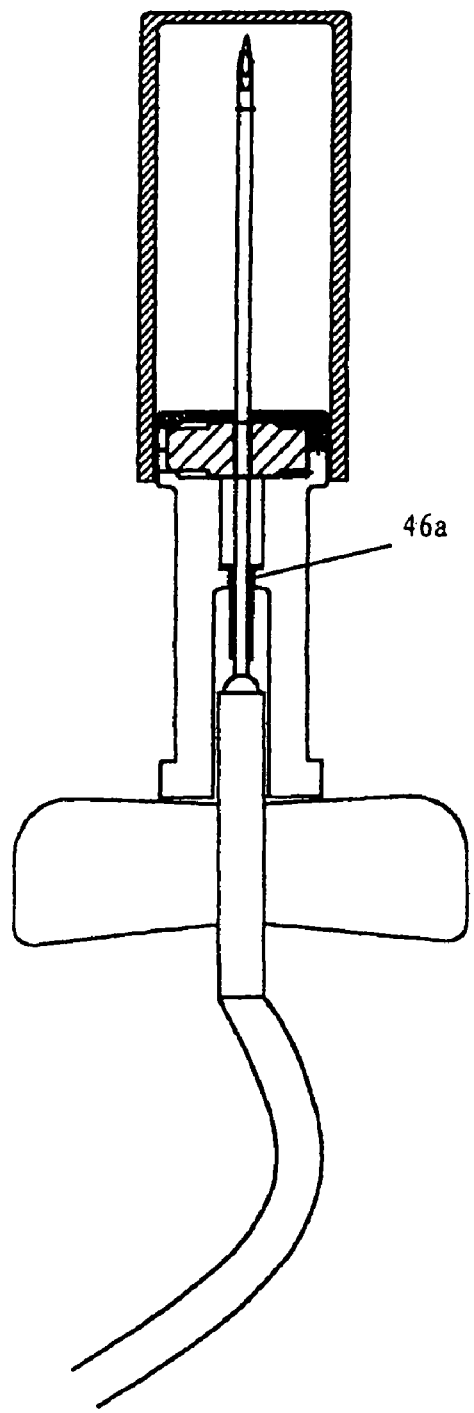
FIGS. 4(a)-(b) show a forth embodiment of the present invention, which is a perfusion needle similar to the third embodiment, except the stop portion of the protecting shell.
Figure 4B:
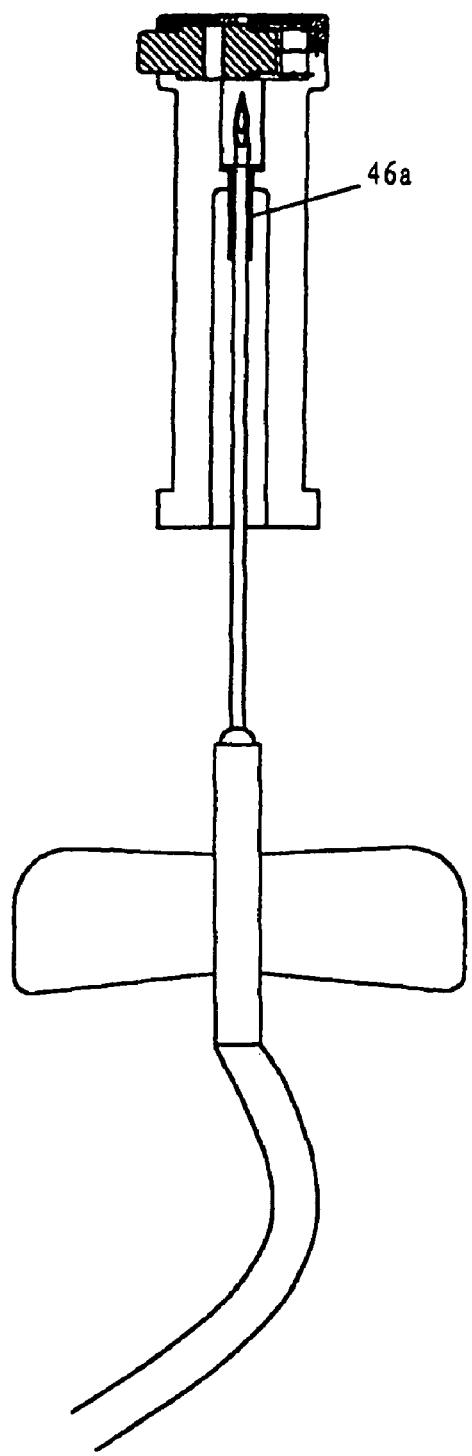

FIGS. 4(*a*)-(*b*) show a fourth embodiment which adopts a sleeve 46a having a turndown side and is similar to the second embodiment of the present invention. Similar to the third embodiment, the fourth embodiment is applied to a perfusion needle.

Figure 5A:
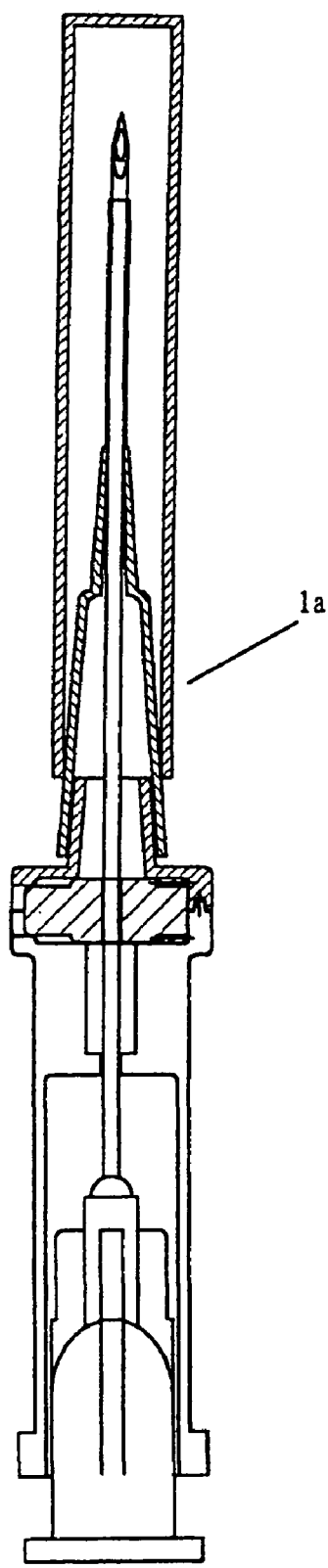
FIGS. 5(a)-(b) show a fifth embodiment of the present invention, which is a indwelling needle.
Figure 5:
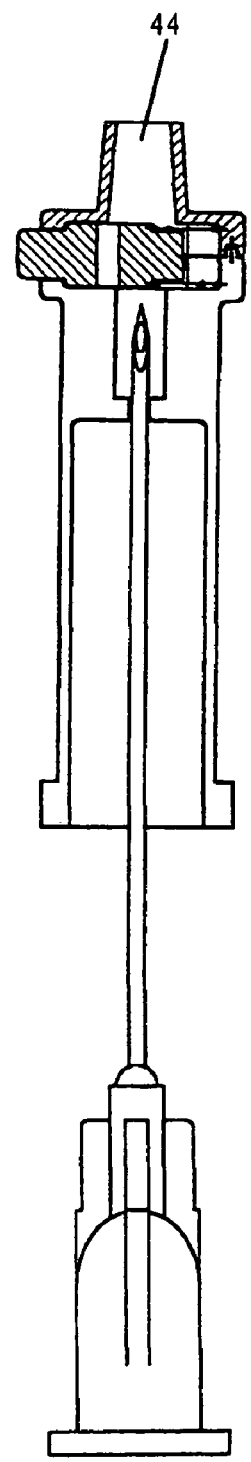

FIGS. 5(*a*)-(*b*) show a fifth embodiment similar to the first embodiment of the present invention. The injector of the first embodiment is generally used in the injection needle for subcutaneous injecting drugs. If the outlet 44 of the safe protecting shell 4 of this embodiment is changed to adapt to match the jacket 1a of the cannula indwelling needle, the medical needle of the present invention can be used in the cannula indwelling needle, as shown in FIGS. 5(*a*)-(*b*).

FIGS. 6(*a*)-(*b*) show a sixth embodiment which adopts a sleeve 46a having a turndown side and is similar to the second embodiment of the present invention. Similar to the fifth embodiment, this embodiment is adapted to a cannula indwelling needle.

The design principles and basic structures of the safe medical needles of the present invention have been illustrated by describing the above six embodiments. The protection scope claimed by this patent application is not limited to these embodiments. Under the condition of not departing from the basic spirit and principles, all any equivalent and similar changes will be involved in the scope of the present invention.

The invention claimed is:

1. A safe medical needle apparatus, comprising:
a needle duct having a needle head and a needle tail;
a needle seat in which the needle tail is installed;
a safe protecting shell through which the needle duct can pass; and
a biasing part through which the needle duct passes;
wherein a protuberant stop portion is provided on an outer surface of the needle duct proximate to the needle head, and a maximum size of cross section of the protuberant stop portion is larger than an outer diameter of remainder of the needle duct;
wherein one end of the safe protecting shell forms an outlet of the needle duct and the other end forms an inlet of the needle duct, the safe protecting shell includes a biasing part cavity adjacent to the outlet, a protecting cavity, cross section of which is smaller than the biasing part cavity and in which the needle head and the protuberant stop portion can move, a stop portion of the safe protecting shell and a needle seat cavity proximate to the inlet of the needle duct and matching the needle seat, sequentially provided between the outlet of the needle duct and inlet of the needle duct of the safe protecting shell, a size of the stop portion of the safe protecting shell is smaller than a maximum size of the stop portion of the needle duct so that the needle duct is movable therein but the stop portion of the needle duct be stopped thereby, and a side of the biasing part cavity has a releasing port; and
wherein the biasing part is elastic and includes a through hole through which the needle duct and the stop portion of the needle duct can pass, under action of an external force, the biasing part is contained in the biasing part cavity of the safe protecting shell and is so biased that the needle duct can pass the through hole, and if the external force is removed, the biasing part is transversally movable towards the releasing port so that the through hole displaces and staggers with the needle duct under action of the elasticity so as to lock the needle duct.

2. The safe medical needle apparatus according to claim 1, wherein the biasing part includes a body of the biasing part made of a non-elastic material and an elastic means connecting to the body of the biasing part, making the through hole of the biasing part displace and stagger with the needle duct.

3. The safe medical needle apparatus according to claim 2, wherein the elastic means is provided between the body of the biasing part and the sidewall of the biasing part cavity.

4. The safe medical needle apparatus according to claim 2, wherein the stop portion of the protecting shell and the protecting shell are formed as a whole.

5. The safe medical needle apparatus according to claim 2, wherein the stop portion of the protecting shell is a sleeve having a contracted neck portion and a turndown side, provided between the safe protecting cavity and the needle seat cavity.

6. The safe medical needle apparatus according to claim 1, wherein the biasing part includes a body of the biasing part made of an elastic material.

7. The safe medical needle apparatus according to claim 6, wherein the stop portion of the protecting shell and the protecting shell are formed as a whole.

8. The safe medical needle apparatus according to claim 6, wherein the stop portion of the safe protecting shell is a sleeve having a contracted neck portion and a turndown side, provided between the protecting cavity and the needle seat cavity.

9. The safe medical needle apparatus according to claim 1, wherein the stop portion of the needle duct is of one of shapes including: circular flange, non-circular flange or at least one protrusion.

* * * * *